US008127926B2

(12) United States Patent
Okada et al.

(10) Patent No.: US 8,127,926 B2
(45) Date of Patent: Mar. 6, 2012

(54) PATCH PACKAGE STRUCTURE

(75) Inventors: Katsuhiro Okada, Osaka (JP); Yoshihiro Iwao, Osaka (JP); Kensuke Matsuoka, Osaka (JP)

(73) Assignee: Nitto Denko Corporation, Osaka (JP)

( * ) Notice: Subject to any disclaimer, the term of this patent is extended or adjusted under 35 U.S.C. 154(b) by 14 days.

(21) Appl. No.: 12/644,160

(22) Filed: Dec. 22, 2009

(65) Prior Publication Data

US 2010/0158991 A1 Jun. 24, 2010

(30) Foreign Application Priority Data

Dec. 22, 2008 (JP) ................................ 2008-324884

(51) Int. Cl.
*A61L 15/16* (2006.01)

(52) U.S. Cl. ........ 206/440; 424/449; 424/448; 604/307; 604/289; 604/301

(58) Field of Classification Search .................. 206/440, 206/441, 460, 447, 484, 582; 424/448, 449; 604/307, 308, 289, 304
See application file for complete search history.

(56) References Cited

U.S. PATENT DOCUMENTS

| | | | | |
|---|---|---|---|---|
| 3,612,265 | A * | 10/1971 | Dickerson | 206/441 |
| 4,687,476 | A * | 8/1987 | Pailin | 604/307 |
| 5,505,306 | A * | 4/1996 | Akemi et al. | 206/438 |
| 5,950,830 | A | 9/1999 | Trigger | |
| 6,120,792 | A * | 9/2000 | Juni | 424/448 |
| 6,617,486 | B1 * | 9/2003 | Murata | 602/48 |
| 6,787,681 | B2 * | 9/2004 | Murakami et al. | 602/57 |
| 2003/0138479 | A1 * | 7/2003 | Mizota et al. | 424/443 |
| 2007/0144928 | A1 * | 6/2007 | Higo et al. | 206/438 |
| 2009/0011159 | A1 * | 1/2009 | Okada et al. | 428/34.1 |
| 2009/0194447 | A1 * | 8/2009 | Okada et al. | 206/440 |
| 2010/0122927 | A1 * | 5/2010 | Matsuoka et al. | 206/438 |

FOREIGN PATENT DOCUMENTS

| | | | |
|---|---|---|---|
| CN | 101219088 | A | 7/2008 |
| EP | 1 944 001 | A1 | 7/2008 |
| EP | 2 011 459 | A1 | 1/2009 |
| JP | 10-310108 | A | 11/1998 |
| JP | 10-511330 | T | 11/1998 |
| JP | 2008-188414 | A | 8/2008 |

(Continued)

OTHER PUBLICATIONS

Office Action issued on Feb. 9, 2011 in counterpart European Application No. 09180088.8.

(Continued)

*Primary Examiner* — David Fidei
(74) *Attorney, Agent, or Firm* — Sughrue Mion, PLLC

(57) ABSTRACT

A patch package structure which includes: a package including a first sheet material which is planar and a second sheet material which has been molded, a peripheral area of the first sheet material having been sealed to a peripheral area of the second sheet material to constitute the package, and a patch disposed in the package; in which the patch includes a backing, a pressure-sensitive adhesive layer formed on at least one side of the backing, and a release liner which protects the pressure-sensitive adhesive surface of the pressure-sensitive adhesive layer, the release liner having a weakening line for assisting a removal of the release liner; and in which the second sheet material has specific first protrudent part, second protrudent part, third protrudent part and elevated part in a central area thereof except the peripheral area thereof.

6 Claims, 6 Drawing Sheets

15
14
b
11
12
a
13

FOREIGN PATENT DOCUMENTS

WO 00/69422 A1 11/2000

OTHER PUBLICATIONS

Extended European Search Report for Application No. 09180088.8-2124, dated Mar. 16, 2010.

Japanese Office Action, dated Apr. 26, 2011, issued in Application No. 2008-324884.

Official Communication issued by the European Patent Office on Jul. 4, 2011 in the corresponding European Patent Application No. 09180088.8.

Chinese Office Action, issued by the State Intellectual Property Office of P.R. China in corresponding Chinese Application No. 200910262221.5 on Sep. 29, 2011.

* cited by examiner

PATCH PACKAGE STRUCTURE

FIELD OF THE INVENTION

The present invention relates to a patch package structure which includes: a package formed by sealing a peripheral area of a first sheet material which is planar to a peripheral area of a second sheet material which has been molded; and a patch disposed in the package.

BACKGROUND OF THE INVENTION

Patches to be applied to the skin for the purpose of, e.g., protecting the affected part and adhesive preparations to be applied to a surface of the skin of a mammal for the purpose of percutaneously administering a drug to the mammal have hitherto been developed.

Such a patch generally includes a backing, a pressure-sensitive adhesive layer formed on at least one side of the backing, and a release liner which protects the pressure-sensitive adhesive surface of the pressure-sensitive adhesive layer. When such a patch is used, the release liner is peeled off. In some patches, the release liner has a weakening line formed therein so as to assist the removal of the release liner. The user utilizes the weakening line for securing a hold for removing the release liner. Namely, the user pinches areas around the weakening line with fingers to remove the release liner.

WO 00/69422 pamphlet describes a patch having a release liner, in which the release liner can be made easily peelable by forming a weakening line of a given shape in a surface of the release liner. However, this patch has the following drawback. Namely, the pressure-sensitive adhesive layer may protrude from or flow out through the weakening line and adhere to inner surfaces of the package in which the patch is placed. There is hence a possibility that it might become difficult to take the patch out of the package or the pressure-sensitive adhesive layer adheres to the hand of the user to give an uncomfortable feeling.

Examples of the techniques for avoiding the adhesion of the pressure-sensitive adhesive layer to inner surfaces of the package include the following. JP-T-10-511330 (the term "JP-T" as used herein means a published Japanese translation of a PCT patent application) discloses a patch package structure in which a patch having a release liner is placed in a blister pack and sealed with a sheet material. A weakening line has been formed in a surface of the release liner of the patch in order to assist the removal of the release liner. This patch package structure disclosed has a given shape so that even when the pressure-sensitive adhesive layer protrudes from an edge of the patch, the adhesive is less apt to adhere to the inner surfaces of the package.

However, since the weakening line of the patch can freely come into contact with the sheet material in this package structure, there is a fear that when the pressure-sensitive adhesive layer protrudes from the weakening line, then the adhesive may adhere to an inner surface of the package to make it difficult to take out the patch or may adhere to the hand of the user to give an uncomfortable feeling.

JP-A-2008-188414 discloses a patch package structure in which a patch having a release liner is disposed so that a weakening line formed in a surface of the release liner faces a planar sheet material. However, even in this patch package structure, the weakening line may still come into contact with the sheet material. There are hence cases where some degree of care is necessary for avoiding the protrusion of the pressure-sensitive adhesive layer through the weakening line.

Recently, soft pressure-sensitive adhesive layers such as pressure-sensitive adhesive layers holding a large amount of a liquid component therein tend to be employed for the purpose of obtaining a soft wear feeling during wear of the patch or reducing the skin irritation caused by separation of the horny layer upon stripping of the patch. With regard to adhesive preparations in which the pressure-sensitive adhesive layer contains a drug, a pressure-sensitive adhesive layer having a larger thickness has been frequently employed in recent adhesive preparations so that the pressure-sensitive adhesive layer can hold a large amount of a drug. In such cases where the pressure-sensitive adhesive layer contains a large amount of a liquid component or the pressure-sensitive adhesive layer is thick, the problem described above is apt to be actualized. There is hence a strong desire for a patch package structure in which a patch can be easily taken out of the package and can be comfortably used.

SUMMARY OF THE INVENTION

In view of the above, an object of the invention is to provide a patch package structure which includes a patch having a weakening line, in which the patch can be easily taken out of the package and comfortably used.

Namely, the present invention provides the following embodiments.

The first embodiment relates to a patch package structure which includes: a package having a first sheet material which is planar and a second sheet material which has been molded, a peripheral area of the first sheet material having been sealed to a peripheral area of the second sheet material to constitute the package, and a patch disposed in the package The patch includes a backing, a pressure-sensitive adhesive layer formed on at least one side of the backing, and a release liner which protects the pressure-sensitive adhesive surface of the pressure-sensitive adhesive layer, the release liner having a weakening line for assisting a removal of the release liner. The second sheet material has the following parts in a central area thereof except the peripheral area thereof: a first protrudent part which projects in the direction opposite to the first sheet material and is located in a position corresponding to the periphery of the patch, a second protrudent part which projects in the direction opposite to the first sheet material and is located in a position corresponding to the weakening line of the patch, a third protrudent part which projects in the direction opposite to the first sheet material and is located in such a position that corresponds to the weakening line of the patch when the patch is disposed in the package after having been rotated at a first angle, and an elevated part which has been elevated above the peripheral area of the second sheet material to a projection height smaller than the projection heights of the first protrudent part, second protrudent part, and third protrudent part in the direction opposite to the first sheet material and is located in a region of the central area other than the first protrudent part, the second protrudent part, and the third protrudent part.

In a second embodiment, the patch is disposed in the package so that the release liner faces the inner surface of the first sheet material.

In a third embodiment, the release liner has a planar outer shape which projects outward from the planar outer shape of the pressure-sensitive adhesive layer.

In a fourth embodiment, the package and the patch each have a planar outer shape which is a substantially regular polygon having n sides and the first angle is 360/n degrees, in which n is a natural number of 3 or larger.

In a fifth embodiment, the patch is an adhesive preparation, the pressure-sensitive adhesive layer of the patch containing a drug.

A sixth embodiment relates to a process for producing a patch package structure, the process including: preparing a patch which includes a backing, a pressure-sensitive adhesive layer formed on at least one side of the backing, and a release liner protecting the pressure-sensitive adhesive surface of the pressure-sensitive adhesive layer, in which the release liner has a weakening line for assisting a removal of the release liner, and sealing a peripheral area of a first sheet material which is planar to a peripheral area of a second sheet material which has been molded to form a package, so that the patch is disposed in the package, where the second sheet material has been molded so as to have the following parts in a central area thereof except the peripheral area thereof: a first protrudent part which projects in the direction opposite to the first sheet material and is located in a position corresponding to the periphery of the patch, a second protrudent part which projects in the direction opposite to the first sheet material and is located in a position corresponding to the weakening line of the patch, a third protrudent part which projects in the direction opposite to the first sheet material and is located in such a position that corresponds to the weakening line of the patch when the patch is disposed in the package after being rotated at a first angle, and an elevated part which has been elevated above the peripheral area of the second sheet material to a projection height smaller than the projection heights of the first protrudent part, second protrudent part, and third protrudent part in the direction opposite to the first sheet material and is located in a region of the central area other than the first protrudent part, the second protrudent part, and the third protrudent part.

The package in the patch package structure of the invention has a given protrudent part (first protrudent part) in a position corresponding to the periphery of the patch. Owing to this constitution, even if the pressure-sensitive adhesive layer protrudes or flows out from the periphery of the patch during the storage of the patch, the pressure-sensitive adhesive layer is less apt to come into contact with the inner surfaces of the package because the periphery of the patch is kept apart from the inner surfaces of the package due to the protrudent part of the molded sheet material of the package.

Furthermore, in the patch package structure of the invention, the release liner of the patch has a weakening line which assists the removal of the release liner, while the molded sheet material of the package has a given protrudent part (second protrudent part) in a position corresponding to the weakening line of the patch. Owing to this constitution, even if the pressure-sensitive adhesive layer protrudes or flows out through the weakening line of the patch during the storage of the patch, the pressure-sensitive adhesive layer is less apt to come into contact with the inner surfaces of the package because the weakening line of the patch is kept apart from the inner surfaces of the package due to the protrudent part of the molded sheet material of the package. Such a protrudent part can inhibit an external stress from being imposed on a region around the weakening line of the patch from outside the package, and this effect is unexpected. Thus, the protrusion or outflow itself of the pressure-sensitive adhesive layer from the patch can be inhibited.

Consequently, the pressure-sensitive adhesive layer of the patch is less apt to adhere to the inner surfaces of the package. Therefore, the patch can be easily taken out of the package, and the uncomfortable feeling of the user due to sticky fingers caused by the pressure-sensitive adhesive layer can be reduced.

In addition, since the molded sheet material of the package has a given elevated part in a region of the central area thereof other than the above-mentioned protrudent parts, the inner surfaces of the two sheet materials constituting the package are kept apart from each other. Therefore, a stress is less apt to be imposed from the package on those areas of the patch except the periphery and weakening line, so that such effect can be enhanced. Moreover, since the elevated part has a projection height smaller than those of the protrudent parts, the elevated part serves as a support for the patch. As a result, the periphery and weakening line of the patch can be inhibited, without fail, from coming into contact with the inner surfaces of the package.

Furthermore, a given protrudent part (third protrudent part) is formed beforehand in such a position that corresponds to the weakening line of the patch when the patch is disposed in the package after being rotated at a given angle. Owing to this constitution, even when the patch is placed in the package after being rotated at a given angle in producing the patch package structure, the same effects as those described above can be obtained.

DESCRIPTION OF REFERENCE NUMERALS

Figure 1A:
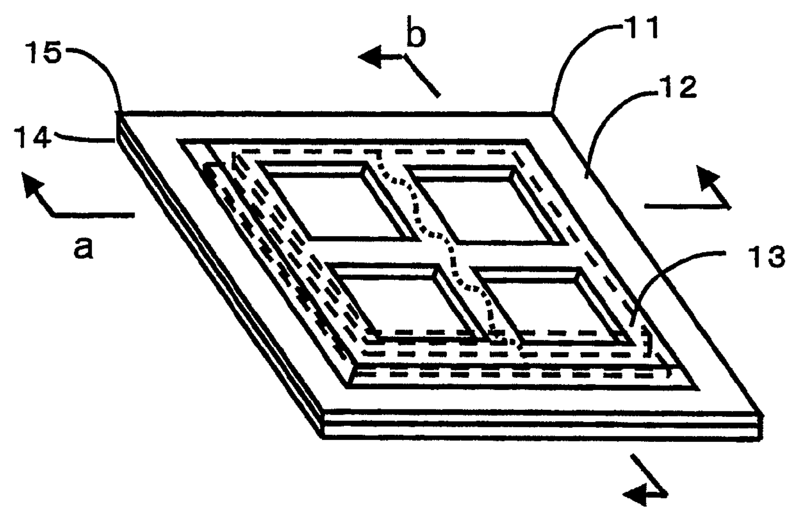
FIGS. 1A to 1C are slant views of one embodiment of the patch package structure of the invention.

11 Patch package structure
12 Package
13 Patch
14 First sheet material
15 Second sheet material
16 Backing
17 Pressure-sensitive adhesive layer
18 Release liner
19 Weakening line
23 Patch
26 Backing
28 Release liner
29 Weakening line
31 Patch package structure
32 Package
33 Patch
35 Second sheet material
39 Weakening line
310 First protrudent part
311 Second protrudent part
312 Third protrudent part
313 Elevated part
42 Package
43 Patch 44 First sheet material
45 Second sheet material
46 Backing
47 Pressure-sensitive adhesive layer
48 Release liner
49 Weakening line
410 First protrudent part
411 Second protrudent part
412 Third protrudent part
413 Elevated part

DETAILED DESCRIPTION OF THE INVENTION

Representative embodiments of the invention are shown below by reference to the drawings. However, the following detailed explanations thereon and specific examples are intended only for exemplification and should not be construed as limiting the scope of the invention. The following explanations on preferred embodiments are merely illustrative and are never intended to limit the invention and the applications or uses thereof.

Explanations are given by reference to the drawings. Incidentally, each drawing are enlarged in the direction perpendicular to the sheet materials (top-and-bottom direction in the drawing) for the purpose of an easy explanation of the concept of the invention. Actual products can be produced in a flatter form. In each drawing, the shapes, pattern, and the like which are visible in the surface are drawn with solid lines, while a shape, pattern, or the like which is invisible in the surface but is necessary for an explanation are drawn with broken lines. The package in each embodiment may be formed so as to have rounded corners to facilitate molding, whereby the frequency of the occurrence of a failure such as, e.g., a pinhole can be reduced.

Figure 1B:
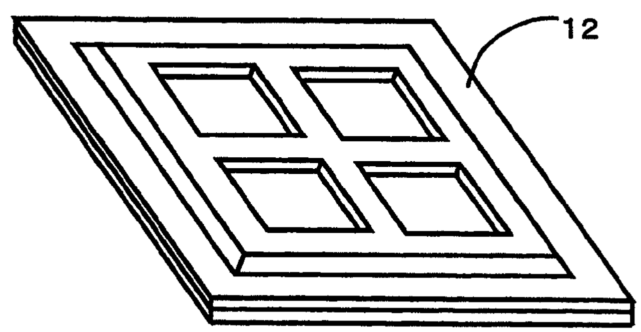

FIG. 1A is a slant view of an embodiment of the patch package structure 11 of the invention. FIG. 1B is a slant view of an example of the package 12, and FIG. 1C is a slant view of an example of the patch 13 to be placed in the package.

With reference to FIG. 1A, the patch package structure 11 of the invention is constituted of: a package 12 formed by sealing a peripheral area of a first sheet material 14 which is planar to a peripheral area of a second sheet material 15 which has been molded; and a patch 13 disposed in the package 12. The package may further contain other substances such as a material for deoxygenation according to the necessity.

Figure 1C:
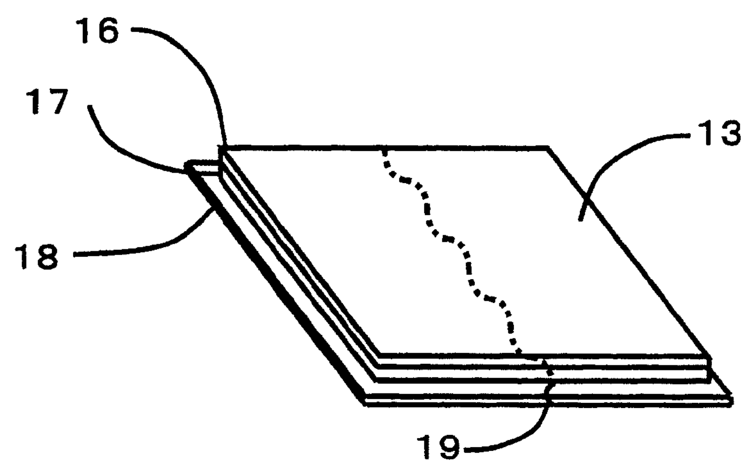

With reference to FIG. 1C, the patch 13 includes a backing 16, a pressure-sensitive adhesive layer 17 formed on at least one side of the backing 16, and a release liner 18 which protects the pressure-sensitive adhesive surface of the pressure-sensitive adhesive layer 17. The release liner has a weakening line 19 for assisting the removal of the release liner. In this example, the release liner 18 has a planar outer shape which projects outward from the planar outer shape of the pressure-sensitive adhesive layer 17. Owing to this constitution, even when the pressure-sensitive adhesive layer protrudes or flows out from an edge (lateral edge) of the pressure-sensitive adhesive layer during the storage of the patch, this pressure-sensitive adhesive layer can be inhibited from adhering to the inner surfaces of the package from the release liner side. With regard to such a projecting planar outer shape of the release liner, the planar outer shape thereof need not project from the whole contour of the planar outer shape of the pressure-sensitive adhesive layer and may partly coincide with the edges of the pressure-sensitive adhesive layer.

With reference to FIG. 1A, the patch 13 in this embodiment is disposed in the package 12 so that the release liner 18 thereof faces the inner surface of the first sheet material 14.

The technical meaning of this will be described later by reference to FIGS. 4A and 4B.

Figure 2A:
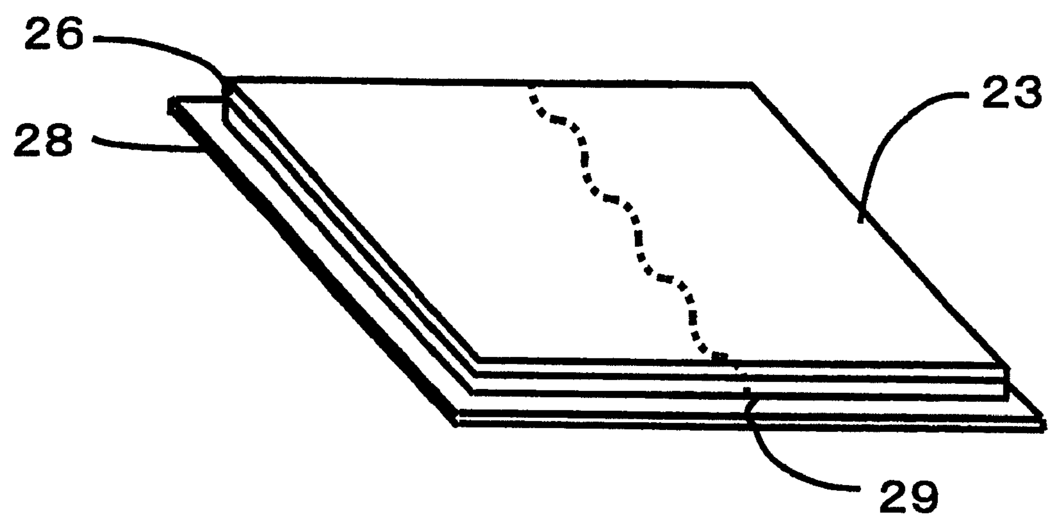
FIGS. 2A and 2B are slant views of an example of the patch in the invention.
Figure 2B:
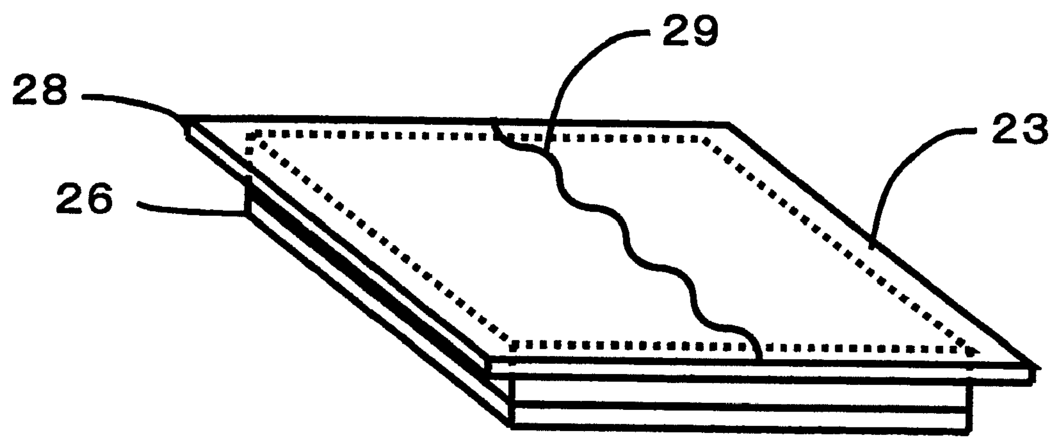

With reference to FIGS. 2A and 2B, FIGS. 2A and 2B are slant views of a patch 23 having a substantially rectangular (in particular, substantially square) planar outer shape. FIG. 2A shows the patch 23, with the backing 26 upper and the release liner 28 lower. FIG. 2B shows the patch 23, with the release liner 28 upper and the backing 26 lower.

In the case of the patch shown in these figures, when the user slightly bends the patch 23 so as to form a ridge along the weakening line 29, then areas suitable for pinching for peeling off the release liner 28 can be easily obtained. This is the reason why such a weakening line 29 is formed in the release liner 28. In this specification, the term "substantially" is intended to allow slight modifications so long as the effects of the invention are produced. For example, the expression "substantially regular polygon having n sides" means that each corner need not be constituted of exactly straight lines only and the shape may include rounded corners. There are tolerances of up to ±5% with respect to the lengths of the sides, angles, etc.

The planar shape of such a weakening line may be a continuous line or a broken line, and the planar shape thereof is not limited to a wavy line. Examples thereof include a substantially straight line and a zigzag line. A wavy line or zigzag line is preferred from the standpoint of easily obtaining pinching areas for peeling off the release liner. The weakening line need not be completely continuous, i.e., may be separated. The weakening line may have uncut areas so long as the uncut areas can be broken with fingers.

Figure 3:
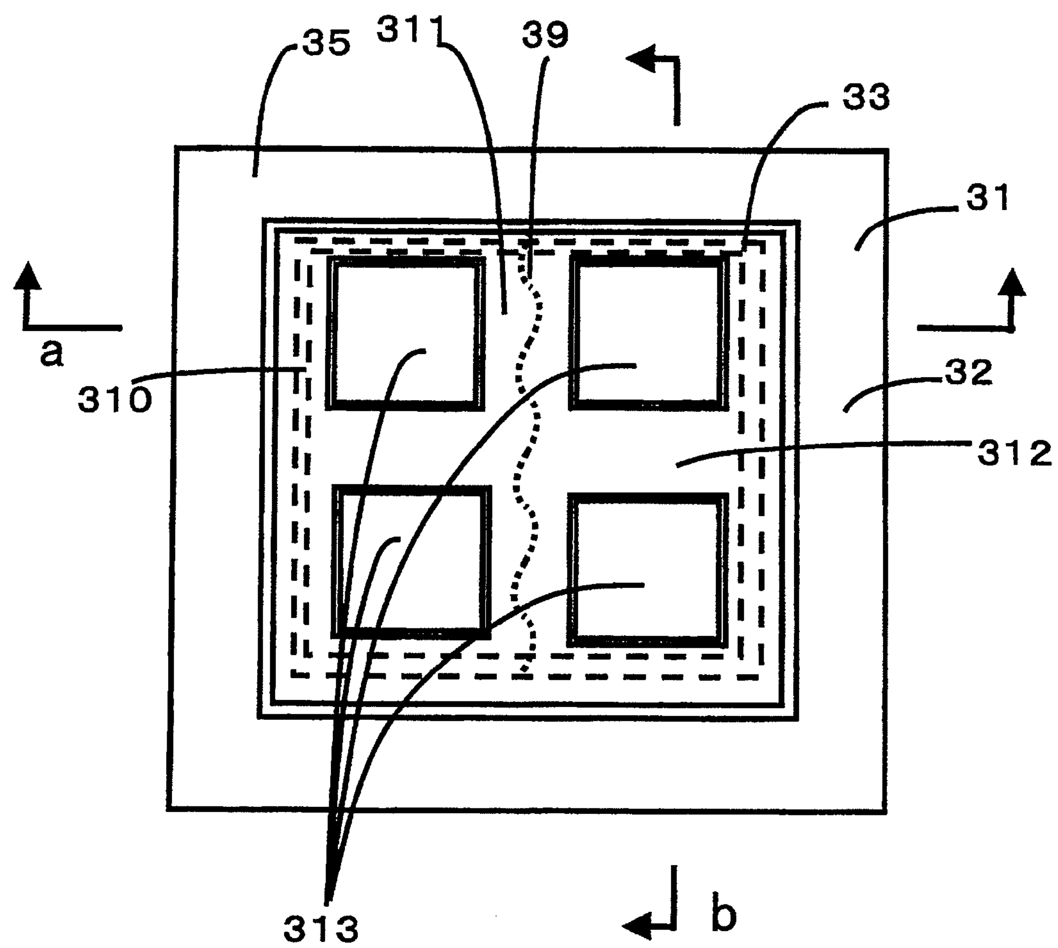
FIG. 3 is a plan view of the embodiment of the patch package structure shown in FIGS. 1A to 1C.

With reference to FIG. 3 next, FIG. 3 is a plan view of the patch package structure shown in FIGS. 1A to 1C. The second sheet material 35 has the following protrudent parts in a central area thereof except the peripheral area. Namely, the second sheet material 35 has: a first protrudent part 310 which projects in the direction opposite to the first sheet material (i.e., in the upward direction perpendicular to the plane of the drawing in FIG. 3) and is located in a position corresponding to the periphery of the patch 33; a second protrudent part 311 which projects in the direction opposite to the first sheet material and is located in a position corresponding to the weakening line 39 of the patch 33; and a third protrudent part 312 which projects in the direction opposite to the first sheet material and is located in such a position that corresponds to the weakening line 39 of the patch 33 when the patch is disposed in the package 32 after being rotated at a first angle (in this embodiment, at an angle of about 90 degrees, i.e., 90±5 degrees). In this specification, the expression "X is located in a position corresponding to Y" means that when the patch having a substantially planar shape and the package are viewed from a vertical direction, the positions of the parts X and Y in those members overlap with each other.

In this embodiment, the second sheet material 35 further has four elevated parts 313 which have been elevated above the peripheral area of the second sheet material 35 in the direction opposite to the first sheet material and are located in regions of the central area of the second sheet material 35 other than the first protrudent part 310, second protrudent part 311, and third protrudent part 312.

There is a case where, in producing the patch package structure, the patch 33 is placed in the package 32 after having been rotated at a first angle, for example, about 90 degrees (90±5 degrees) in the embodiment shown in FIG. 3. In such a case, if the second sheet material 35 of the package does not have the third protrudent part 312, this means that the second sheet material 35 of the package 32 has no protrudent part in the position corresponding to the weakening line 39 of the patch 33. There is hence a possibility in this case that the pressure-sensitive adhesive layer might protrude or flow out through the weakening line 39 and adhere to an inner surface of the package 32.

Figure 4A:
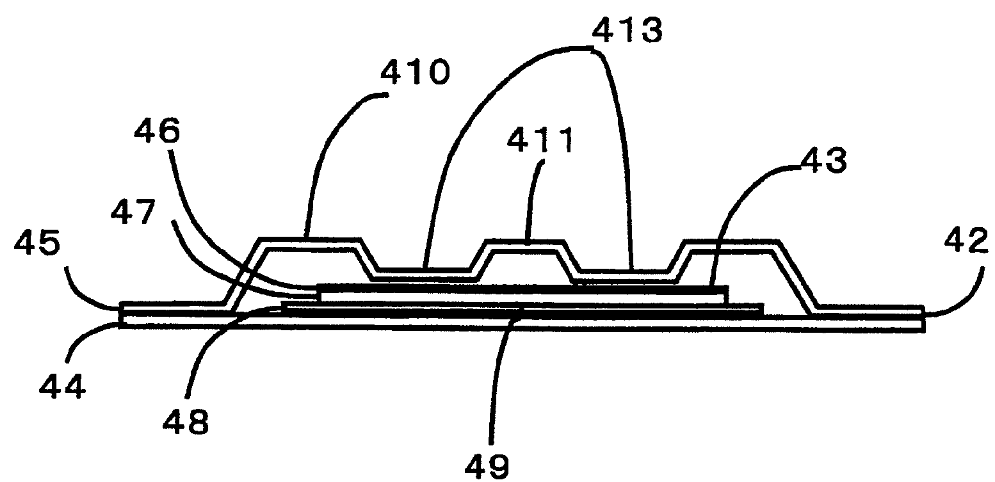
FIGS. 4A and 4B are sectional views of the embodiment of the patch package structure shown in FIGS. 1A to 1C.
Figure 4B:
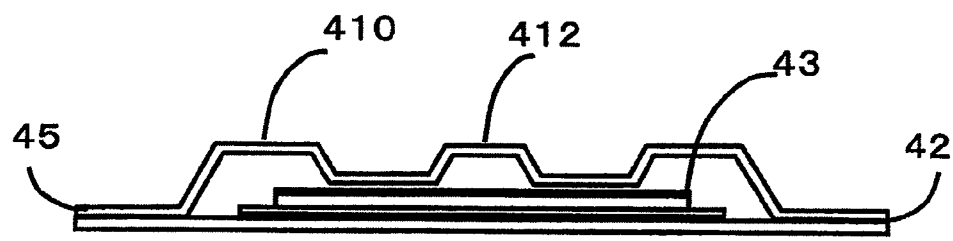

With reference to FIG. 4 next, FIGS. 4A and 4B are sectional views of the patch package structure shown in FIGS. 1A to 1C. FIG. 4A is a sectional view taken on the line indicated by the arrows a in FIG. 1A or by the arrows a in FIG. 3. FIG. 4B is a sectional view taken on the line indicated by the arrows b in FIG. 1A or by the arrows b in FIG. 3.

With reference to FIG. 4A first, a patch 43 is disposed in a package 42 formed by sealing a peripheral area of a first sheet material 44 which is planar to a peripheral area of a second sheet material 45 which has been molded. The second sheet material 45 has been molded so as to have, in a central area thereof except the peripheral area thereof, a first protrudent part 410 which projects in the direction opposite to the first sheet material 44 and is located in a position corresponding to the periphery of the patch 43. In addition, the second sheet material 45 has been molded so as to have a second protrudent part 411 which projects in the direction opposite to the first sheet material 44 and is located in a position corresponding to the weakening line 49 of the patch 43. Furthermore, the second sheet material 45 has, in a central area thereof except the peripheral area thereof, elevated parts 413 which have been elevated above the peripheral area of the second sheet material 45 in the direction opposite to the first sheet material 44 and are located in regions of the central area other than the first protrudent part 410, the second protrudent part 411, and the third protrudent part which will be described later by reference to FIG. 4B.

Since the second sheet material 45 has such elevated parts 413, the inner surfaces of the first sheet material 44 and second sheet material 45 constituting the package 42 are kept apart from each other. As a result, a stress is less apt to be imposed from the package 42 on those areas of the patch 43 except the periphery thereof and weakening line 49. In addition, these elevated parts 413 in the second sheet material 45 have a projection height smaller than those of the protrudent parts. Therefore, the elevated parts 413 serve as a support for the patch 43, whereby an edge of the pressure-sensitive adhesive layer 47 in the periphery of the patch 43 can be inhibited from coming into contact with the inner surface of the package 42 at the first protrudent part 410 from the backing 46 side. Furthermore, as in the embodiment shown in this figure, it is preferred that the patch 43 is disposed in the package 42 so that the release liner 48 thereof faces the first sheet material 44 and that the release liner 48 has a planar outer shape which projects outward from the planar outer shape of the pressure-sensitive adhesive layer 47. In this case, an edge of the pressure-sensitive adhesive layer 47 in the periphery of the patch 43 can be inhibited from coming into contact with the inner surface of the first sheet material 44 from the release liner side. However, in the embodiment shown in FIGS. 1A to 1C, the patch 13 may be disposed in the package 12 so that the backing 16 thereof faces the inner surface of the first sheet material 14.

With reference to FIG. 4B next, the second sheet material 45 in the package 42 has a third protrudent part 412 besides the first protrudent part 410. In the case where the patch is disposed in the package in the state shown in FIGS. 1A to 1C and FIG. 3, this patch 43 does not have a weakening line 49 in the position corresponding to the third protrudent part 412. However, once the patch is rotated at a first angle and then disposed in the package, the third protrudent part 412 can function as a protrudent part located in a position corresponding to the weakening line 419.

The plane-direction shape of the patch package structure shown in FIGS. 1A to 4B is not particularly limited. Examples of the planar outer shape of the patch (including the backing, pressure-sensitive adhesive layer, and release liner) and that of the package independently include substantially polygonal shapes such as substantially triangular shapes and substantially quadrangular shapes, e.g., substantially rectangular shapes, elliptic shapes, circular shapes, and other various shapes. From the standpoint of the efficiency of utilizing the space in the package in which the patch is disposed, it is preferred that the planar outer shape of the patch and that of the package are similar to each other. From the standpoint of diminishing material discard to effectively utilize materials, the planar outer shapes of the patch and package preferably are a substantially quadrangular shape such as a substantially rectangular shape. In particular, when the planar outer shapes of the patch and package are substantially square, it is easy to form beforehand a given protrudent part in a position that corresponds to the weakening line of the patch when the patch is disposed in the package after having been rotated at a given angle. Consequently, in producing the patch package structure, even if the patch is placed in the package after having been erroneously rotated at an angle of about 90 degrees (e.g., 90±5 degrees), the pressure-sensitive adhesive layer can be inhibited from adhering to the inner surfaces of the package.

Figure 5:
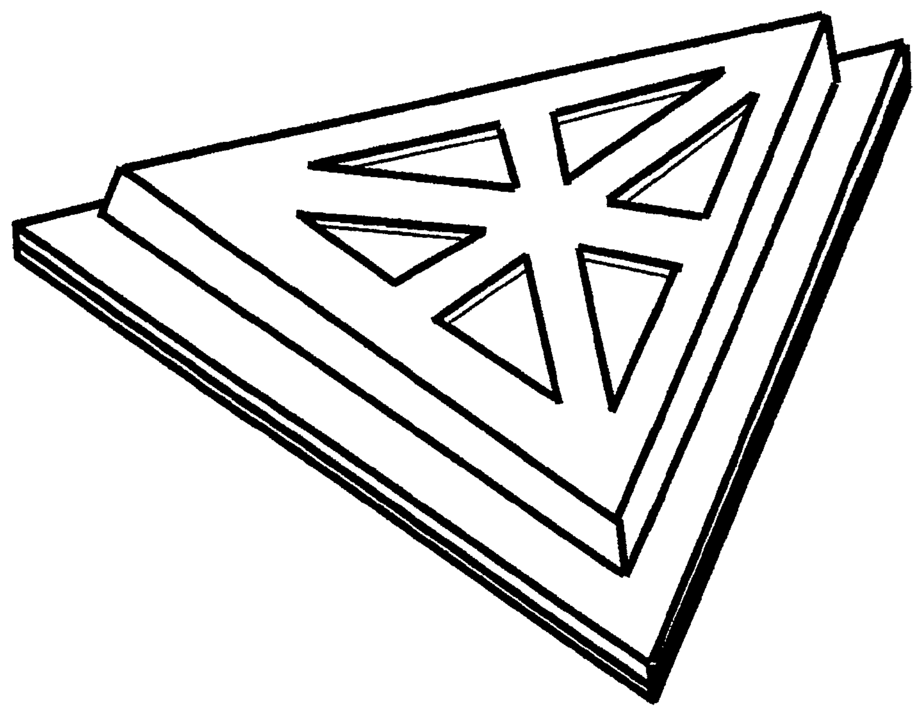
FIG. 5 is a slant view of another embodiment of the patch package structure of the invention.

However, the patch, package, and patch package structure can have other planar outer shapes. From the standpoint of obtaining the above-mentioned effect when the patch is placed in the package after having been erroneously rotated at a first angle, the planar outer shapes thereof preferably are substantially regular polygons having n sides (wherein n is a natural number of 3 or larger). Examples of such polygons include a substantially regular triangle, substantially square shape, substantially regular pentagon, substantially regular hexagon, substantially regular heptagon, and substantially regular octagon. The first angle is 360/n degrees. Since the patch can be rotated in two directions, the patch package structure having a planar outer shape which is a substantially regular polygon having n sides generally need to have two or more third protrudent parts. In the case where the patch package structure has a substantially square planar outer shape and the patch is rotated at an angle of about 90 degrees in each of the two directions, then the weakening line comes to be located in the same position. Consequently, one third protrudent part suffices. That outer planar shape is therefore advantageous from the standpoint of facilitating the molding of the package, and this effect is unexpected. In FIG. 5 is shown a slant view of an embodiment in which the patch, package, and patch package structure each are a substantially regular triangle.

Figure 6:
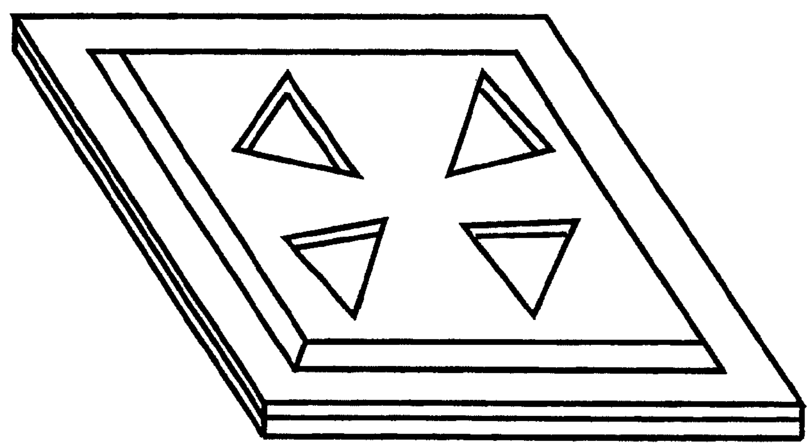
FIG. 6 is a slant view of still another embodiment of the patch package structure of the invention.
Figure 7:
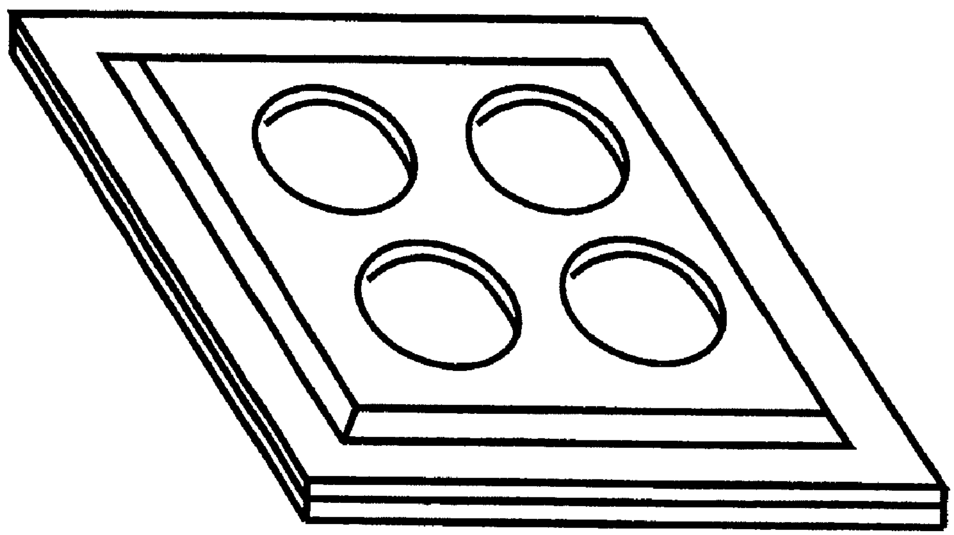
FIG. 7 is a slant view of a further embodiment of the patch package structure of the invention.
Figure 8:
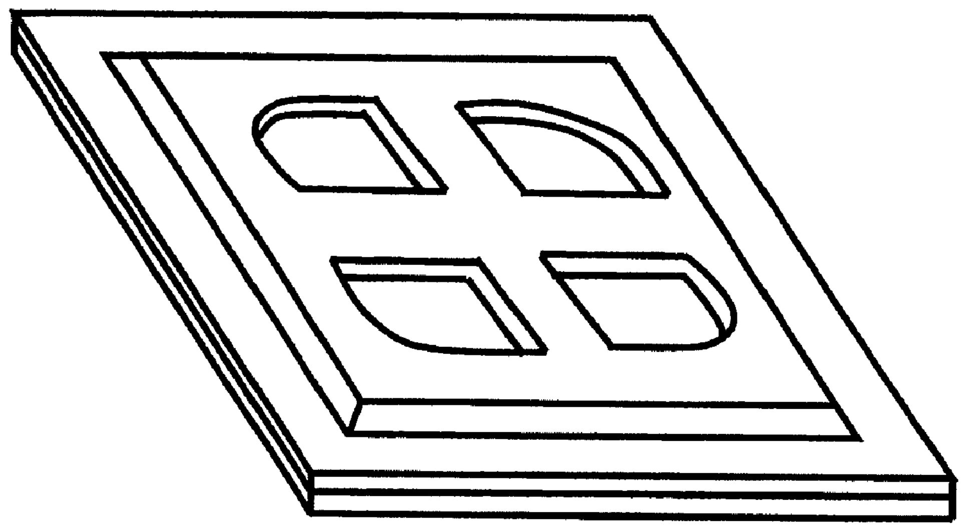
FIG. 8 is a slant view of still a further embodiment of the patch package structure of the invention.

The planar outer shape of each elevated part is not particularly limited. Examples thereof include substantially square shapes such as those shown in FIGS. 1A to 4B, substantially regular polygons, e.g., substantially triangular shapes such as those shown in FIG. 5 and FIG. 6, shapes defined by a curve, e.g., substantially circular shapes such as those shown in FIG. 7, and combination of these such as those shown in FIG. 8. From the standpoint of ease of molding, it is preferred that the planar outer shape of each elevated part is a shape including part of a substantial square, such as a substantially square shape and a shape (shown in FIG. 8) formed by modifying a substantially square shape by replacing one vertex and adjoining segments with a part of an arc.

Specific examples of the size and shape of each of components and parts in the embodiment shown in FIGS. 1A to 4B are as follows. The planar outer shapes of the backing and pressure-sensitive adhesive layer of the patch are a substantially rectangular shape (in particular, substantially square shape) in which one side has a length of 20-100 mm and another side has a length of 20-100 mm. The planar outer shape of the release liner is a substantially rectangular shape (in particular, substantially square shape) in which one side has a length of 22-104 mm and another side has a length of 22-104 mm. Consequently, the release liner in this embodiment has a strip-shaped projecting peripheral area having a width of 1-2 mm. The planar shape of the first protrudent part is a frame shape constituted of strips having a width of 2-20 mm. The planar shape of the second protrudent part is a strip shape having a width of 2-20 mm. The planar shape of the third protrudent part is a strip shape having a width of 2-20 mm. The projection heights of these protruded parts in the second sheet material are 0.5-3 mm in terms of height from the peripheral area of the second sheet material. The shape of each elevated part is a substantially rectangular shape (in particular, substantially square shape) in which one side has a length of 2-50 mm and another side has a length of 2-50 mm. The projection height thereof in the second sheet material is 0.3-2 mm in terms of height from the peripheral area of the second sheet material.

The first sheet material and second sheet material in the patch package structure of the invention described above are not particularly limited so long as both materials can be sealed together for forming the package. Heat-sealable sheet materials are preferred from the standpoint of ease of production. Examples of such packaging materials include films of resins such as polyolefins including polyethylene and polypropylene, polyesters including poly(ethylene terephthalate), and other resins including poly(vinyl chloride) and polyacrylonitrile, metal films such as aluminum foils, materials obtained by vapor-depositing aluminum on these films, and laminated films obtained by laminating two or more thereof.

From the standpoints of impermeability to package contents such as a drug and heat sealability, a polyacrylonitrile film or the like is preferred for use as such a packaging material. From the standpoint of the property of not adsorbing package contents such as a drug, it is preferred to employ a polyester, in particular, poly(ethylene terephthalate) or the like. From the standpoint of the property of being impermeable to or not transmitting package contents, light rays, or gases, more preferred packaging materials are those resin films which have undergone aluminum vapor deposition and laminated films obtained by laminating an aluminum foil to those resin films. More preferred from the standpoint of reconciling those properties are laminated films obtained by laminating a polyester, in particular poly(ethylene terephthalate), with a polyacrylonitrile film. Most preferred is a laminated film obtained by laminating a polyester, in particular poly(ethylene terephthalate), with an aluminum foil or vapor-deposited aluminum layer and a polyacrylonitrile film. From the standpoint of the storage stability of package contents such as a drug, a laminated film obtained by laminating a water-impermeable layer and a water-permeable layer respectively to the outer side and inner side of a hygroscopic layer containing a drying agent is also preferred.

Materials and constitutions of the first sheet material and the second sheet material may be the same or different. The first sheet material is preferably made of a flexible material so that the first sheet material can be easily sealed with the second sheet material to thereby facilitate production. The second sheet material is preferably made of a rigid material because the second sheet material has been molded in a given shape.

The thickness of the first sheet material is not particularly limited. However, it is preferably 10-200 μm, more preferably 20-100 μm, from the standpoints of production efficiency and impermeability to ingredients to be packaged in the package structure. The thickness of the second sheet material is not particularly limited. It is, however, preferred that the second sheet material have some degree of stiffness because of the necessity of retaining the given shape. From this standpoint, the thickness thereof is preferably 50-300 μm, more preferably 50-200 μm.

Molding methods for obtaining the second sheet material having the given shape are not limited. Examples thereof include vacuum/pressure forming, injection molding, and press molding. From the standpoints of suitability for cost reduction, degree of freedom of shapes, material selection, etc., vacuum forming, pressure forming, and the like are preferred.

The patch may be an adhesive preparation in which the pressure-sensitive adhesive layer contains a drug. The drug herein is not particularly limited. Preferred is a drug which can be administered to a mammal such as a human being through the skin, i.e., which is percutaneously absorbable. Examples of such drugs include systemic anesthetics, hypnotic/sedative agents, antiepileptics, antipyretic/analgesic/antiphlogistic agents, antidizzying agents, psychoneurotics, local anesthetics, skeletal muscle relaxants, agents for autonomous nerve, antispasmodics, anti-Parkinsonian agents, antihistamines, cardiotonics, antiarrhythmics, diuretics, antihypertensives, vasoconstrictors, coronary vasodilators, peripheral vasodilators, antiarteriosclerotic agents, agents for circulatory organs, respiration facilitators, antitussive/expectorant agents, hormone drugs, external-use preparations for purulent diseases, analgesic/antipruritic/astringent/antiphlogistic agents, agents for parasitic skin diseases, hemostats, antipodagrics, agents for diabetes, antineoplastics, antibiotics, chemotherapeutics, narcotics, and smoking renunciation aids.

The content of the percutaneously absorbable drug is not particularly limited so long as it sufficiently produces the effect thereof and does not impair the adhesiveness of the pressure-sensitive adhesive. However, the content thereof in the pressure-sensitive adhesive is, for example, 0.01-70% by weight, preferably 0.1-60% by weight, more preferably 0.5-40% by weight. In case where the content thereof is lower than 0.01% by weight, there is a possibility that the remedial effect might be insufficient. In case where the content thereof is higher than 70% by weight, there is a possibility that skin irritation might occur and such a large drug amount might be economically disadvantageous.

The pressure-sensitive adhesive layer contains a pressure-sensitive adhesive. The pressure-sensitive adhesive is not particularly limited. Examples thereof include acrylic pressure-sensitive adhesives containing an acrylic polymer; rubber-based pressure-sensitive adhesives such as styrene/diene/styrene block copolymers (e.g., styrene/isoprene/styrene block copolymers and styrene/butadiene/styrene block copolymers), polyisoprene, polyisobutylene, and polybutadiene; silicone type pressure-sensitive adhesives such as silicone rubbers, dimethylsiloxane-based polymers, and diphenylsiloxane-based polymers; vinyl ether type pressure-sensitive adhesives such as poly(vinyl methyl ether), poly(vinyl ethyl ether), and poly(vinyl isobutyl ether); vinyl ester type pressure-sensitive adhesives such as vinyl acetate/ethylene copolymers; and polyester type pressure-sensitive adhesives produced from a carboxylic acid ingredient such as dimethyl terephthalate, dimethyl isophthalate, or dimethyl phthalate and a polyhydric alcohol ingredient such as ethylene glycol.

Acrylic pressure-sensitive adhesives or rubber-based pressure-sensitive adhesives are preferred among such pressure-sensitive adhesives because acrylic or rubber-based pressure-sensitive adhesives give a pressure-sensitive adhesive layer which is capable of holding a liquid component therein and hence can give a soft feeling during wear on the skin. In particular, acrylic pressure-sensitive adhesives are preferred because they can be easily crosslinked and give a pressure-sensitive adhesive layer capable of holding a large amount of a liquid component therein.

Examples of the acrylic pressure-sensitive adhesives include acrylic ester type pressure-sensitive adhesives containing as the main component a polymer comprising monomer units derived from one or more $C_{2-18}$ alkyl esters of (meth)acrylic acid. Examples of the rubber-based pressure-sensitive adhesives include rubber-based pressure-sensitive adhesives containing as the main component at least one member selected from polyisobutylene, polyisoprene, and styrene/diene/styrene copolymers.

The liquid component is not particularly limited. From the standpoint of compatibility with the pressure-sensitive adhesive layer, organic liquid components are preferred. Although the organic liquid components are not particularly limited, those having the effect of accelerating percutaneous absorption are preferred. Examples of such organic liquid ingredients include glycols such as ethylene glycol, diethylene glycol, propylene glycol, triethylene glycol, polyethylene glycol, and polypropylene glycol; fats and oils such as olive oil, caster oil, squalane, and lanolin; hydrocarbons such as liquid paraffin; various surfactants; ethoxy stearyl alcohol; glycerol monoesters such as oleic acid monoglyceride, caprylic acid monoglyceride, and lauric acid monoglyceride, glycerol diesters, glycerol triesters, and mixtures thereof; alkyl esters of fatty acids, such as ethyl laurate, isopropyl myristate, isotridecyl myristate, octyl palmitate, isopropyl palmitate, ethyl oleate, and diisopropyl adipate; higher fatty acids such as oleic acid and caprylic acid; and other compounds including N-methylpyrrolidone and 1,3-butanediol.

In the case where a liquid component is contained in the pressure-sensitive adhesive layer, there is a possibility that during storage of the patch, the pressure-sensitive adhesive layer might protrude from or flow out through the weakening line formed in the release liner. The invention is advantageously practiced especially in such a case. From this standpoint, the content of the liquid component in the pressure-sensitive adhesive layer is preferably 5-70% by weight, more preferably 10-65% by weight, most preferably 15-60% by weight.

When the pressure-sensitive adhesive layer is relatively thick, the protrusion or outflow of the pressure-sensitive adhesive layer from the weakening line tends to occur. The invention is advantageously practiced especially in such a case. From this standpoint, the thickness of the pressure-sensitive adhesive layer is preferably 20-300 μm, more preferably 30-250 μm, most preferably 50-200 μm.

The explanations of the invention are merely illustrative, and modified embodiments thereof which do not depart from the spirit of the invention are hence intended to be within the scope of the invention. Such modified embodiments should not be construed as departing from the spirit and scope of the invention.

This application is based on Japanese patent application No. 2008-324884 filed Dec. 22, 2008, the entire contents thereof being hereby incorporated by reference.

What is claimed is:

1. A patch package structure which comprises:

a package comprising a first sheet material which is planar and a second sheet material which has been molded, a peripheral area of the first sheet material having been sealed to a peripheral area of the second sheet material to constitute the package, and a patch disposed in the package;

wherein the patch comprises a backing, a pressure-sensitive adhesive layer formed on at least one side of the backing, and a release liner which protects the pressure-sensitive adhesive surface of the pressure-sensitive adhesive layer, the release liner having a weakening line for assisting a removal of the release liner; and wherein the second sheet material has the following parts in a central area thereof except the peripheral area thereof:

a first protrudent part which projects in the direction opposite to the first sheet material and is located in a position corresponding to the periphery of the patch, a second protrudent part which projects in the direction opposite to the first sheet material and is located in a position corresponding to the weakening line of the patch, a third protrudent part which projects in the direction opposite to the first sheet material and is located in a position that intersects the second protrudent part at an angle of 360/n degrees, wherein n is a natural number of 3 or more, at a position corresponding to the center of the weakening line of the patch, wherein each protrudent part has a projection height, and an elevated part which has been elevated above the peripheral area of the second sheet material to a projection height smaller than the projection heights of the first protrudent part, second protrudent part, and third protrudent part in the direction opposite to the first sheet material and is located in a region of the central area other than the first protrudent part, the second protrudent part, and the third protrudent part.

2. The package structure according to claim 1, wherein the patch is disposed in the package so that the release liner faces the inner surface of the first sheet material.

3. The package structure according to claim 1, wherein the release liner has a planar outer shape which projects outward from the planar outer shape of the pressure-sensitive adhesive layer.

4. The patch package structure according to claim 2, wherein the package and the patch each have a planar outer shape which is a substantially regular polygon having n sides and the first angle is 360/n degrees, in which n is a natural number of 3 or larger.

5. The package structure according to claim 1, wherein the patch is an adhesive preparation, the pressure-sensitive adhesive layer of the patch containing a drug.

6. A process for producing a patch package structure, the process comprising:

preparing a patch which comprises a backing, a pressure-sensitive adhesive layer formed on at least one side of the backing, and a release liner protecting the pressure-sensitive adhesive surface of the pressure-sensitive adhesive layer, in which the release liner has a weakening line for assisting a removal of the release liner, and sealing a peripheral area of a first sheet material which is planar to a peripheral area of a second sheet material which has been molded to form a package, so that the patch is disposed in the package, wherein the second sheet material has been molded so as to have the following parts in a central area thereof except the peripheral area thereof:

a first protrudent part which projects in the direction opposite to the first sheet material and is located in a position corresponding to the periphery of the patch, a second protrudent part which projects in the direction opposite to the first sheet material and is located in a position corresponding to the weakening line of the patch, a third protrudent part which projects in the direction opposite to the first sheet material and is located in a position that intersects the second protrudent part at an angle of 360/n degrees, wherein n is a natural number of 3 or more, at a position corresponding to the center of the weakening line of the patch, wherein each protrudent part has a projection height, an elevated part which has been elevated above the peripheral area of the second sheet material to a projection height smaller than the projection heights of the first protrudent part, second protrudent part, and third protrudent part in the direction opposite to the first sheet material and is located in a region of the central area other than the first protrudent part, the second protrudent part, and the third protrudent part.

* * * * *